(12) United States Patent
Teoh

(10) Patent No.: US 10,850,068 B2
(45) Date of Patent: Dec. 1, 2020

(54) CATHETER DEVICES WITH VALVES AND RELATED METHODS

(71) Applicant: B. Braun Melsungen AG, Melsungen (DE)

(72) Inventor: Hui Kuun Teoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 181 days.

(21) Appl. No.: 15/110,060

(22) PCT Filed: Jan. 8, 2015

(86) PCT No.: PCT/EP2015/050262
§ 371 (c)(1),
(2) Date: Jul. 6, 2016

(87) PCT Pub. No.: WO2015/104336
PCT Pub. Date: Jul. 16, 2015

(65) Prior Publication Data
US 2016/0331937 A1    Nov. 17, 2016

Related U.S. Application Data

(60) Provisional application No. 61/924,865, filed on Jan. 8, 2014.

(51) Int. Cl.
*A61M 25/06* (2006.01)
*A61M 39/06* (2006.01)
(Continued)

(52) U.S. Cl.
CPC .... *A61M 25/0606* (2013.01); *A61M 25/0097* (2013.01); *A61M 25/0618* (2013.01);
(Continued)

(58) Field of Classification Search
CPC .......... A61M 25/0606; A61M 25/0097; A61M 25/0618; A61M 2025/0089; A61M 39/06;
(Continued)

(56) References Cited

U.S. PATENT DOCUMENTS 5,009,391 A * 4/1991 Steigerwald ...... A61M 39/0613
137/849
5,613,663 A * 3/1997 Schmidt ................ A61M 39/26
251/149.2
(Continued)

FOREIGN PATENT DOCUMENTS

CN    101808692 A    8/2010
CN    102355923 A    2/2012
(Continued)

OTHER PUBLICATIONS

Office Action on corresponding foreign application (CN Application No. 201580012787.6) from the National Intellectual Property Administration dated Mar. 27, 2019.
(Continued)

*Primary Examiner* — Kevin C Sirmons
*Assistant Examiner* — Tezita Z Watts
(74) *Attorney, Agent, or Firm* — Klein, O'Neill & Singh, LLP

(57) ABSTRACT

Needle assemblies and related methods are disclosed having a needle hub with a needle, a catheter tube with a catheter hub and having the needle extending through the catheter tube; and a valve positioned in an interior cavity of the catheter hub, the valve having a first section with a first chord, a second chord, and a plurality of slits defining a plurality of flaps, a second section attached to the first section, and a third section attached to the first section; an inside edge formed on the second section and pressed against the first section; an inside edge formed on the third
(Continued)

section and pressed against the first section; and wherein a first flow path is provided adjacent the first chord and a second flow path is provided adjacent the second chord.

21 Claims, 7 Drawing Sheets

(51) Int. Cl.
*A61M 25/00* (2006.01)
*A61M 39/24* (2006.01)

(52) U.S. Cl.
CPC ............ *A61M 39/06* (2013.01); *A61M 39/24* (2013.01); *A61M 2025/0089* (2013.01); *A61M 2039/062* (2013.01); *A61M 2039/064* (2013.01); *A61M 2039/0653* (2013.01); *A61M 2039/246* (2013.01); *A61M 2039/2426* (2013.01); *A61M 2207/00* (2013.01)

(58) Field of Classification Search
CPC ............ A61M 39/24; A61M 2039/062; A61M 2039/064; A61M 2039/06053; A61M 2039/2426; A61M 2039/246; A61M 2039/0626; A61M 2039/0666; A61M 2207/00

See application file for complete search history.

(56) References Cited

U.S. PATENT DOCUMENTS

| 5,624,395 | A | 4/1997 | Mikhail et al. |
| 2005/0148823 | A1 | 7/2005 | Vaugh et al. |
| 2006/0155245 | A1* | 7/2006 | Woehr ............ A61M 39/0693 604/164.08 |
| 2011/0046570 | A1 | 2/2011 | Stout et al. |
| 2013/0253443 | A1 | 9/2013 | Woehr et al. |
| 2014/0276434 | A1 | 9/2014 | Woehr et al. |

FOREIGN PATENT DOCUMENTS

| EP | 2213327 A1 | 8/2010 |
| JP | H11-319115 A | 11/1999 |
| JP | 2012-517326 A | 8/2012 |
| JP | 2016-509916 A | 4/2016 |

OTHER PUBLICATIONS

Office Action on corresponding foreign application (CN Application No. 201580012787.6) from the National Intellectual Property Administration dated May 22, 2020.
Office Action on corresponding foreign application (JP Application No. 2016-545325) from the Japanese Patent Office dated May 8, 2018.
International Search Report and Written Opinion on corresponding PCT application (PCT/EP2015/050262) from International Searching Authority (EP) dated Apr. 22, 2015.
Decision of Rejection on corresponding foreign application (JP Application No. 2016-545325) from the Japanese Patent Office dated Sep. 25, 2018.
Office Action on corresponding foreign application (EP Application No. 15700203.1) from the European Patent Office dated Oct. 12, 2017.
Supplementary Examination Report on corresponding foreign application (SG Application No. 11201605546U) from the Intellectual Property Office of Singapore dated Sep. 1, 2016.
Notice of Eligibility for Grant on corresponding foreign application (SG Application No. 11201605546U) from the Intellectual Property Office of Singapore dated Sep. 20, 2016.
First Examination Report on related foreign application (IN Application No. 201617024317) from Intellectual Property India dated Oct. 8, 2020.

* cited by examiner

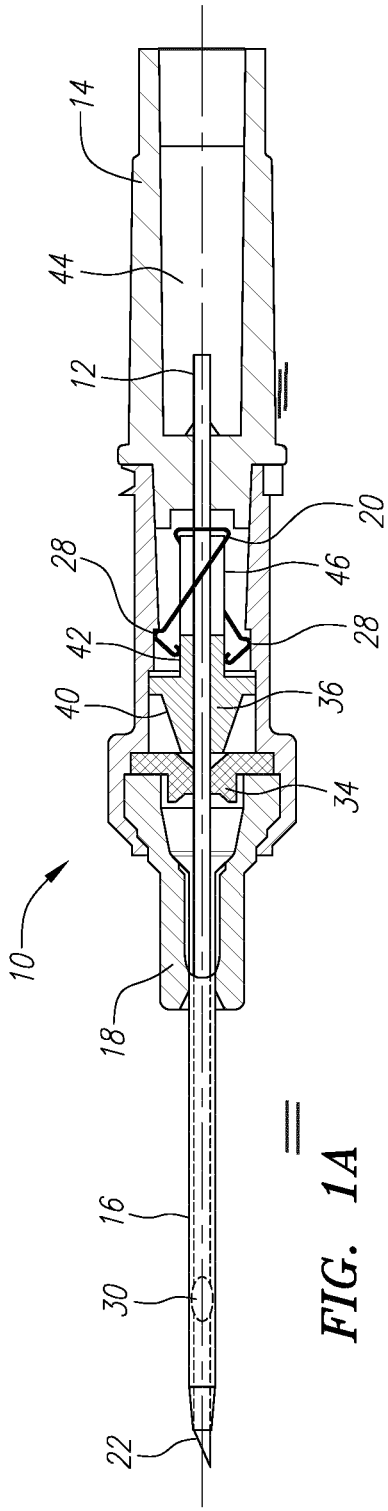
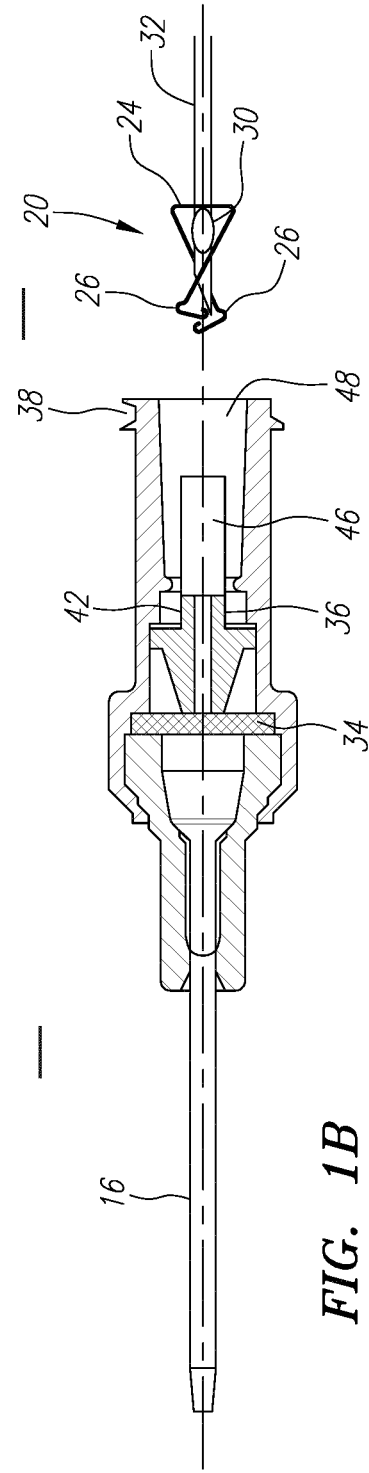
FIG. 1A
FIG. 1B

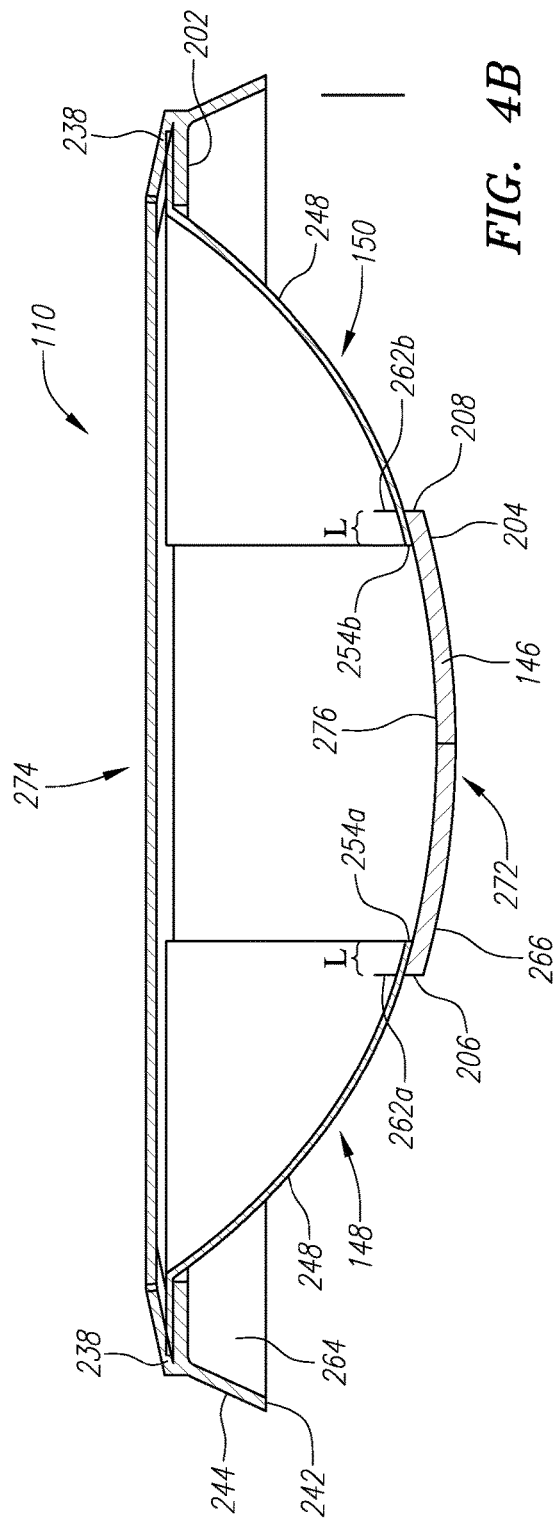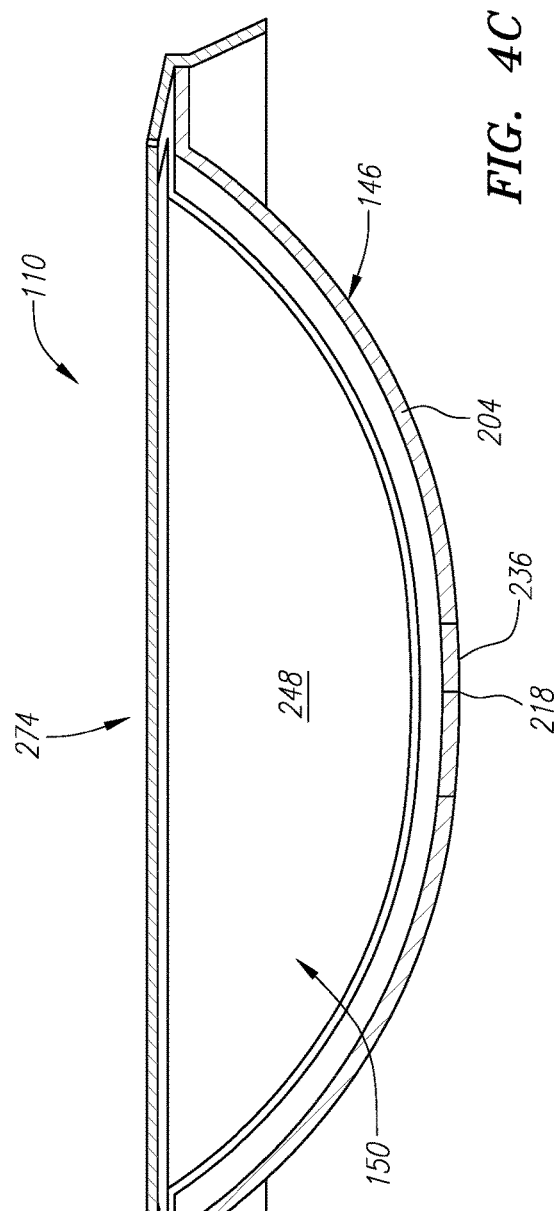

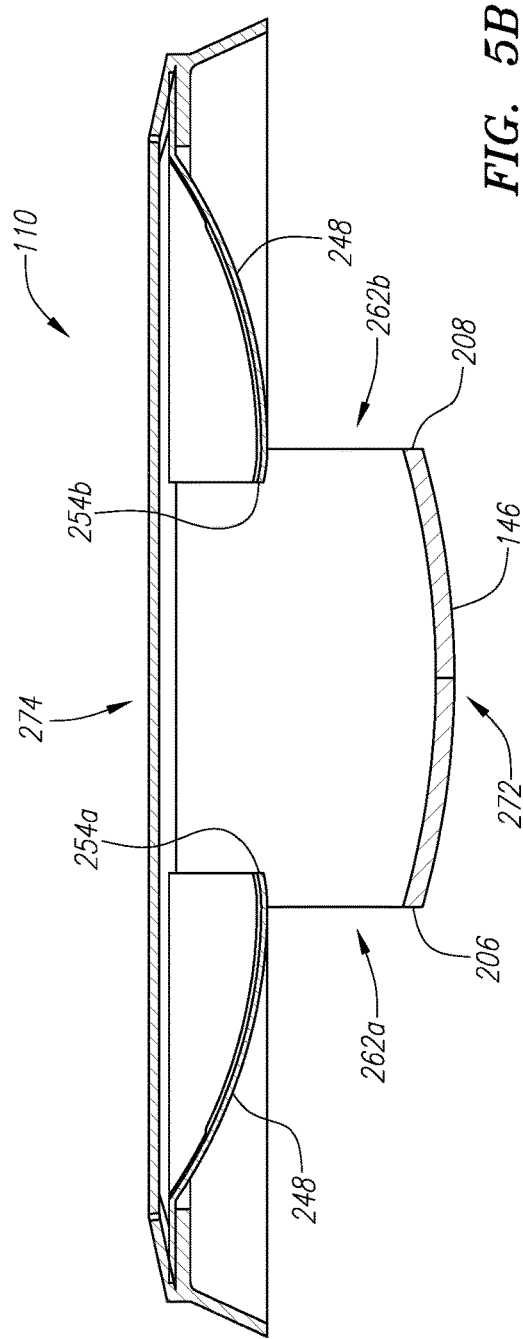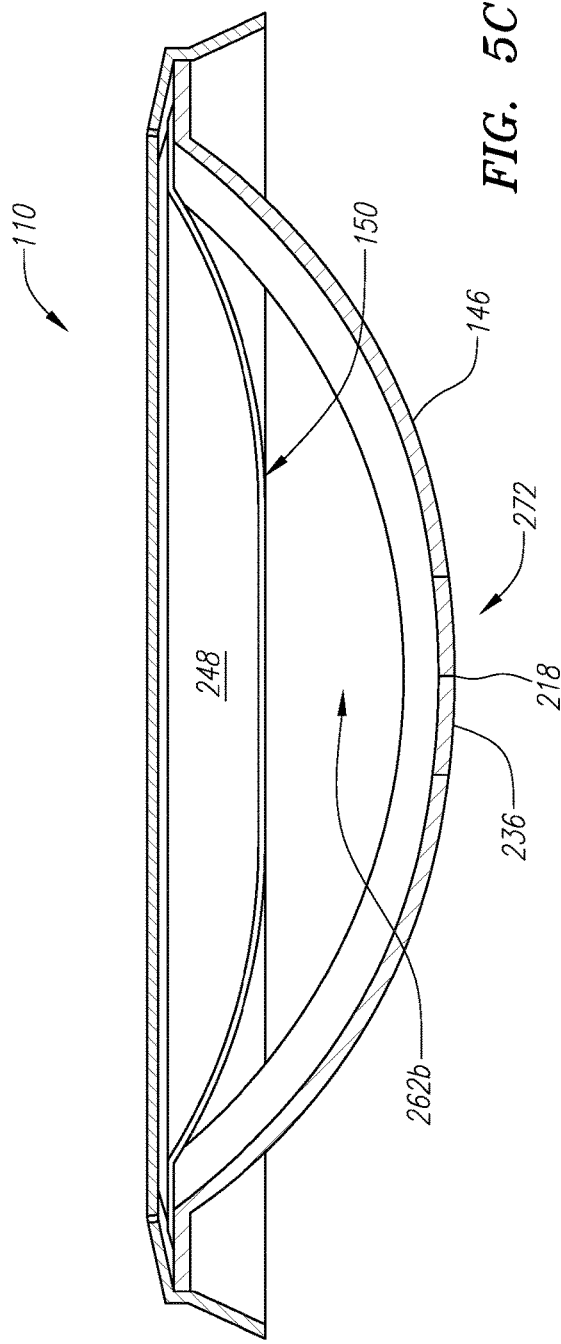

CATHETER DEVICES WITH VALVES AND RELATED METHODS

FIELD OF ART

The disclosed invention generally relates to intravenous (IV) infusion devices, including IV catheters. In particular, IV catheter assemblies having a multi section control valve using different flexible sections of the valve to control the flow of blood and infusion fluids are disclosed.

BACKGROUND

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing to the catheter. Blood control catheters include an internal blood control valve that is opened by the insertion of a male Luer or other object into a proximal end of the catheter adapter. Non-limiting examples of blood control valves are disclosed in United States Patent Application Publication No. 2011/0046570, filed Aug. 20, 2009, titled "Systems and Methods for Providing a Flushable Catheter Assembly." Following placement of the catheter into the vasculature of a patient, an IV fluid source can be connected to the catheter adapter or catheter hub, opening the blood control valve. Thus connected, fluid from the IV source can begin flow into a patient through the catheter.

As is well known in the art, typical blood pressure is 10 to 20 centimeters of water. Infusion bags are usually placed about 100 cm above the patient's heart to direct flow into the patient. At roughly that height, the pressure exerted by the fluid from the infusion bag is much greater than the blood pressure of the patient and therefore can flow into the patient.

Some catheter adapters permit verification of proper placement of the catheter in the blood vessel before fluid infusion begins, such as by providing a flashback chamber of the catheter assembly where a "flashback" of blood can be observed. To confirm flashback in catheter assemblies that do not include a blood control valve, a clinician must manually occlude the vein to prevent undesirable exposure to blood. In contrast, blood control valves can eliminate the need for such manual occlusion, while also reducing the likelihood of blood exposure during catheter placement.

SUMMARY

A needle assembly comprising: a needle hub; a needle extending from a distal end of the needle hub; a catheter tube attached to a catheter hub and having the needle extending through the catheter tube; and a valve positioned in an interior cavity of the catheter hub, said valve comprising a first section comprising a first chord, a second chord, and a plurality of slits defining a plurality of flaps, a second section attached to the first section, and a third section attached to the first section; an inside edge formed on the second section and pressed against the first section; an inside edge formed on the third section and pressed against the first section; and wherein a first flow path is provided adjacent the first chord and a second flow path is provided adjacent the second chord.

The needle assembly wherein the valve can be formed from at least two different materials.

The needle assembly wherein the valve can comprise three slits.

The needle assembly wherein the three slits can form three independently movable flaps.

The needle assembly wherein the inside edge formed on the second section can form an edge of a first deflectable flap portion and the inside edge formed on the third section can form an edge of a second deflectable flap portion.

The needle assembly wherein part of the inside edge of the first deflectable flap portion and part of the inside edge of the second deflectable flap portion can be displaced from a first position to a second position when the valve is in an open position.

The needle assembly wherein the material of the first section can be more rigid than the material of the second and third sections.

The needle assembly wherein the first deflectable flap portion can overlap with the first chord and the second deflectable flap portion can overlap with the second chord in a closed position.

The needle assembly can further comprise a needle guard located inside the catheter hub, said needle guard can be sized and shaped to cover a needle tip on the needle in a protective position.

A method of manufacturing a needle assembly comprising: forming a needle hub and attaching a needle to the needle hub; attaching a catheter tube to a catheter hub, said catheter hub comprising an interior cavity; placing a valve comprising a first section comprising a first chord, a second chord, and a second section comprising a first deflectable flap portion, and a third section comprising a second deflectable flap portion in the interior cavity of the catheter hub; placing the needle through the first section of the valve and the catheter tube; and wherein the first deflectable flap portion has an inner edge in contact with the first section adjacent the first chord and defining a first flow path and the second deflectable flap portion has an inner edge in contact with the first section adjacent the second chord defining a second flow path.

The method wherein the valve can be formed from at least two different materials.

The method wherein the first section of the valve can comprise three slits sized and shaped to allow the needle to pass through.

The method wherein the material of the first section can be more rigid than the material of the second and third sections.

The method can further comprise placing a needle guard over the needle to cover a needle tip of the needle in a protective position.

The method can further comprise placing a male medical implement into a proximal opening of the catheter hub and using only fluid pressure to open the first flow path and the second flow path.

A needle assembly comprising: a needle hub; a needle extending from a distal end of the needle hub; a catheter tube sized and shaped to contain the needle prior to and during venipuncture; a catheter hub distal of the needle hub and comprising a first section and a second section, the first section being distal of the second section; and a valve disk comprising a first section comprising a first chord, a second chord, and a second section comprising a first flap portion, and a third section comprising a second flap portion; wherein the first flap portion moves from a first position pressed against the first chord to a second position out of contact with the first chord, and the second flap portion moves from a first position pressed against the second chord to a second position out of contact with the second chord.

The needle assembly wherein the valve disk can be formed from at least two different materials.

The needle assembly wherein the valve disk can comprise three slits.

The needle assembly wherein the material of the first section can be more rigid than the material of the second and third sections.

The needle assembly wherein the second section and the third section can both overlap the first section.

The needle assembly wherein the second section and the third section can join the first section at the overlapping portions.

The needle assembly wherein the slits can seal after the needle is removed therefrom.

BRIEF DESCRIPTION OF THE DRAWINGS

These and other features and advantages of the present device, system, and method will become appreciated as the same becomes better understood with reference to the specification, claims and appended drawings wherein:

FIG. 1A shows a side cross section of a needle assembly in a ready to use position;

FIG. 1B shows a side cross section of the needle assembly with the needle and needle hub withdrawn from the catheter hub and the catheter tube and the needle and/or needle guard in a protective position;

FIG. 4B shows a top cross section view of the valve of FIG. 4A;

FIG. 4C shows a side cross section view of the valve of FIG. 4A;

FIG. 5B shows a top cross section view of the valve of FIG. 5A; and

FIG. 5C shows a side cross section view of the valve of FIG. 5A.

DETAILED DESCRIPTION

Figure 2:
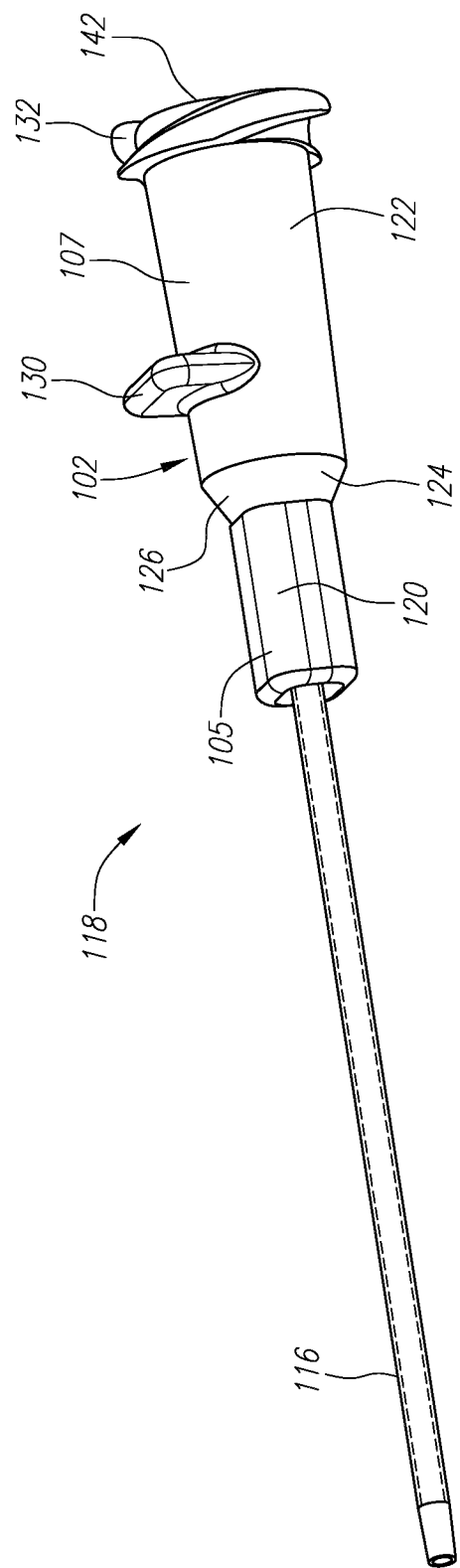
FIG. 2 shows a perspective view of an embodiment of a catheter hub and catheter tube.

The detailed description set forth below in connection with the appended drawings is intended as a description of the presently preferred embodiments of catheter assemblies with control valves provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

FIGS. 1A and 1B show one embodiment of a needle assembly 10 comprising a needle 12, needle hub 14, a catheter tube 16, and a catheter hub 18. Some embodiments of the device may include a needle guard 20 for covering the needle in a used position, making the assembly a safety needle assembly. As shown, a needle guard 20 is provided to cover a tip 22 of the needle 12 after the needle is withdrawn following successful venipuncture. The exemplary needle guard 20 can comprise a proximal wall 24 having an opening for slidably receiving the needle 12, two arms 26 extending distally of the proximal wall 24, and a distal wall 28 located on each arm for blocking the needle tip 22. The two arms can intersect one another when viewed from a side and can have different lengths so that the distal walls 28 are offset. The needle guard 20, such as the perimeter defining the opening on the proximal wall 24, can interact with the change in profile on the needle shaft 32, which can be a bulge or a crimp, to prevent the guard from displacing distally off of the needle.

The change in profile 30 on the needle has a different profile than a nominal diameter of the needle shaft, which can include a crimp, a bulge, a recess, or combinations thereof, near the needle tip 22, for interacting with the needle guard 20. The needle shaft 32 is connected at or near its proximal end to the needle hub 14 and typically has a blunt end extending into the flash chamber 44 of the needle hub. Following successful venipuncture, the needle hub 14 is separated from the catheter hub 18, withdrawing the needle 12 from the catheter hub and the catheter tube and engaging the needle guard 20, if one is incorporated. The catheter tube 16 remains in the punctured vasculature. Blood flows through the catheter tube and into the catheter hub 18. This process is well known in the art and commonly referred to as flashback. Within the catheter hub 18, flow of fluid through the catheter hub may be stopped by blocking the path of the fluid with a structure, for example, a valve or a septum.

As shown in FIGS. 1A and 1B, the needle assembly 10 includes a valve 34, a valve opener 36 with a conical shaped distal end 40, a cylindrical stub 42 extending in a proximal direction, at least one leg extension or actuator element 46, exterior threads 38, and a two-piece or two-part catheter hub 18. Those skilled in the art will understand that a needle assembly may be made with or without all of these elements, and that the catheter hub may be unitarily formed as a one-piece catheter hub. For example, a catheter hub 18 may include a valve without a valve opener, and that the two piece catheter hub may be unitarily formed as a one piece catheter hub with the valve wedged into a valve seat. The proximal hub opening 48 is sized and shaped to receive a male medical implement, such as a Luer tip, a syringe tip, or a Luer adaptor. The needle guard 20 may be axially located next to the at least one leg extension 46 or between two leg extensions if two are incorporated. Once the guard 20 is removed, a male medical implement, such as a male Luer tip, may be inserted in through the proximal opening 48 of the catheter hub to advance the actuator or opener 36 to then open the valve 34. In some examples, a valve is incorporated without a valve actuator or opener. Once such valve is disclosed herein that can be manipulated to open by fluid pressure only, without an actuator or opener.

FIG. 2 shows a perspective view of an exemplary catheter hub 118 without the needle or needle hub for clarity, such as following successful venipuncture and the catheter tube 116 is placed into the patient's vein. The catheter hub 118 comprises a hub body or body 102, a relatively smaller cylindrical section or nose section 105 and a relatively larger cylindrical section 107 located proximally of the smaller diameter cylindrical section 105. The larger cylindrical section has a diameter greater than that of the smaller cylindrical section, and in some embodiments, a greater length. In other embodiments the cylindrical sections 105, 107 have the same length or the smaller section may be longer than the larger section. Both the smaller and larger cylindrical sections comprise wall elements 120, 122. The smaller and larger cylindrical sections are hollow, with bores formed by their respective wall elements and sized and shaped to accommodate a valve, a valve opener, a tip protector, a male medical implement, or combinations thereof. A tab 130 is provided on the exterior surface of the large cylindrical section 107 to facilitate gripping. Near the open proximal end 142 of the larger cylindrical section are external threads 132. Preferably the proximal opening 142 of the hub body 102 is formed to ISO standards for a female Luer for receiving a male Luer. Other fitting types or shapes are contemplated for receiving a male implement at the proximal opening.

A transition 124 connects the smaller cylindrical section 120 to the larger cylindrical section 122. The transition comprises a wall element 126 with an exterior that angles radially outward from the diameter of the smaller cylindrical section 120 to the larger cylindrical section 122. The transition comprises an interior bore 128 (FIG. 3) formed by an interior of the wall element 126. The bore 128 at the transition roughly parallels the angle of the exterior, and the bore receives a retainer 134 (FIG. 3) for retaining the catheter tube 116 to the catheter hub 118, as further discussed below.

Figure 3:
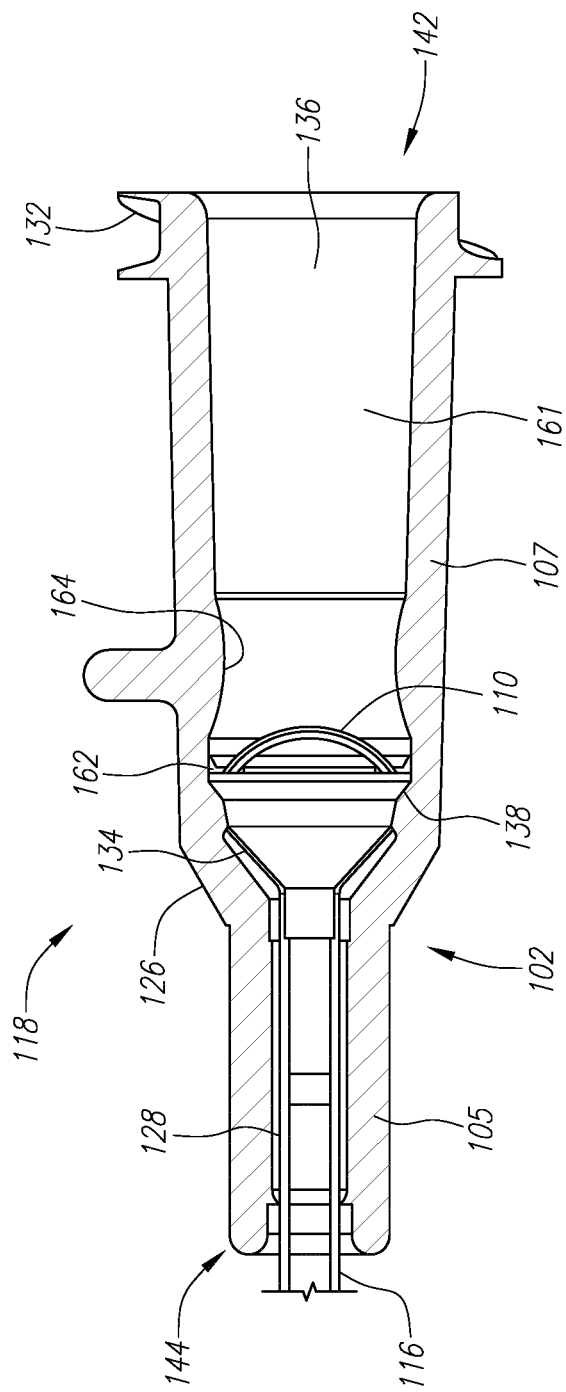
FIG. 3 shows a side cross section of an embodiment of a catheter device with a multi-hardness valve.

FIG. 3 shows a detail partial cross sectional view of the catheter hub 118 of the present disclosure. The catheter tube 116 extends internally through a bore 128 of the smaller cylindrical section 105 and is retained to the catheter hub by a funnel shaped retainer 134, which is conventional. The funnel shaped retainer generally matches the inside dimension of the transition 124. A distal end of the bore 136 of the large cylindrical section 107 includes a shoulder 138 against which a valve 110 is mounted, which may alternatively be referred to as simply a membrane. In the example shown, the valve 110 is positioned in a receiving space 162 defined in part by the shoulder 138. As shown, the receiving space 162 in a recessed space having an inside diameter (ID) of a larger dimension than the ID at the shoulder 138 or the ID at an interior projection or ring 164, if incorporated to interact with a needle guard 20, as an example. The location of the ring 164 can be adjusted in the axial direction of the catheter hub 118 to interact with the needle guard, such as to provide a gripping surface for the needle guard during retraction of the needle after the vasculature is punctured. The receiving space 162 may have shaped wall surfaces, such as a taper surface or another shoulder, to accommodate the geometry of the perimeter of the valve 110. In service, from the open proximal end 142, fluid flows distally, passing through the valve 110 and into the smaller diameter distal cylindrical section 105. From there, fluid flows into the catheter tube 116 attached to the distal end 144 of the smaller diameter cylindrical section 105 and into the patient. The manner in which the valve 110 can be manipulated to restrict or permit fluid flow is further discussed below.

Figure 4A:
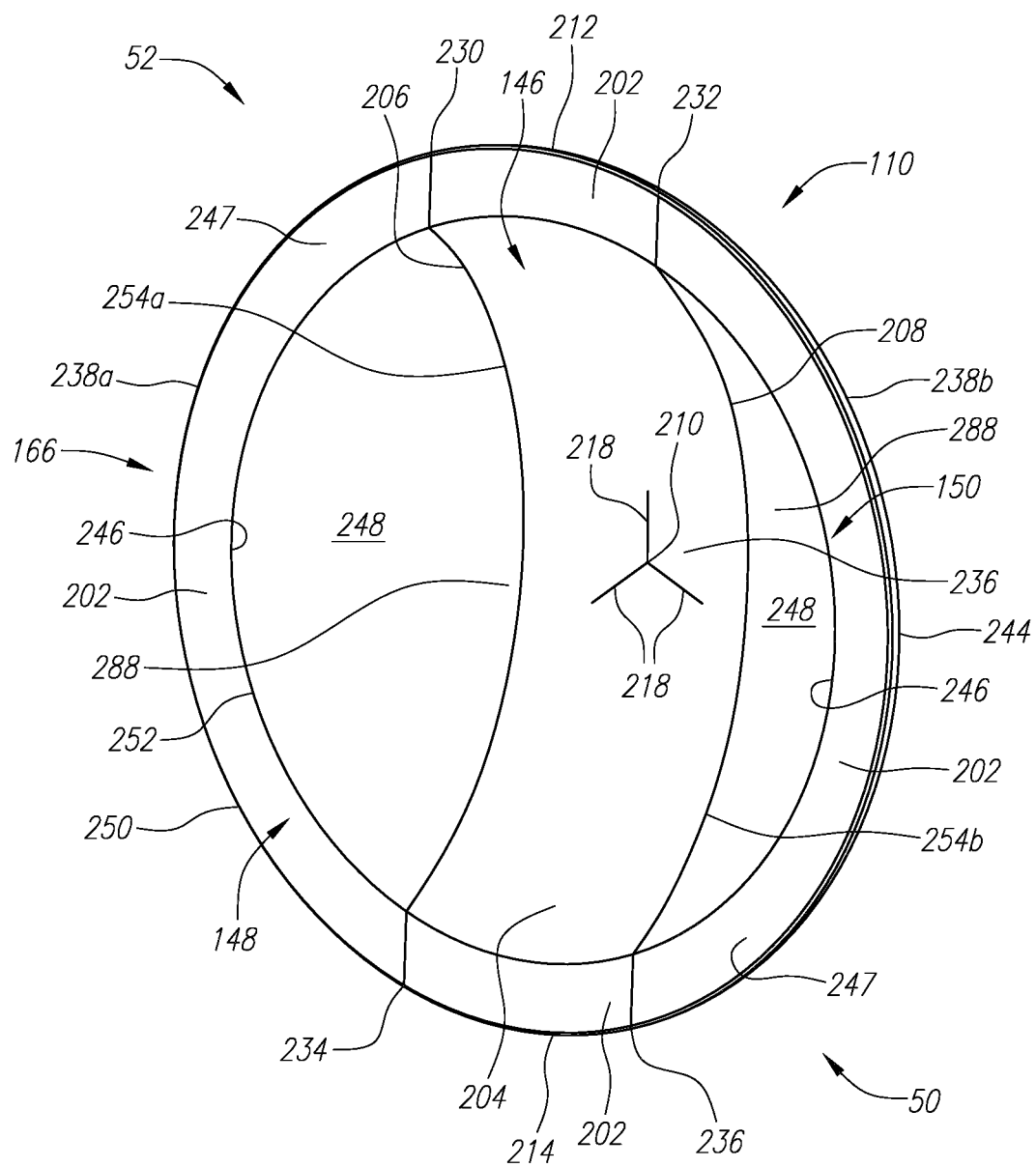
FIG. 4A shows a detailed perspective view of a valve having multiple different flexible sections for use to control fluid flow through a catheter hub, similar to that shown in FIG. 3.
Figure 5A:
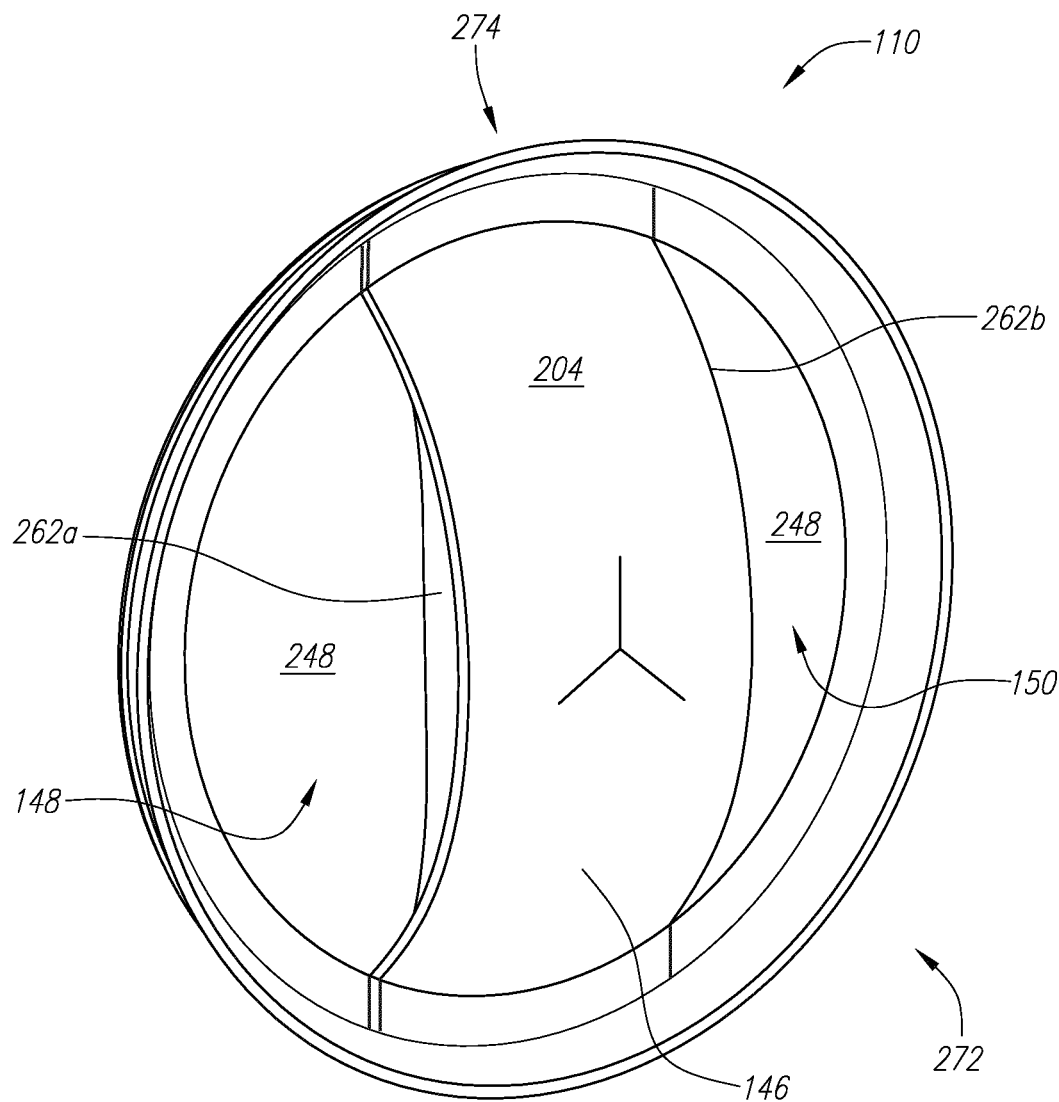
FIG. 5A shows a detailed perspective view of the valve of FIG. 4A in an open position.

With reference now to FIGS. 4A-C, the valve 110 in accordance with aspects of the present disclosure is shown, which is usable inside a catheter hub to control flow thereacross, such as that shown in FIG. 3. FIGS. 5A-5C show the same valve in an open position, such as when a male Luer adapter or an IV adapter is inserted into the proximal opening of the catheter hub and fluid is permitted to flow into the catheter hub to open the valve. The valve 110, which can comprise a disk shape, comprises a valve body 166 comprising a first section 146, a second section 148, and a third section 150. The first section 146 is located generally in the center or mid part of the valve body 166 and is formed from a relatively more rigid structure and/or material than the structure or material(s) of the second section 148 and the third section 150, which are relatively more flexible and elastic than the material of the first section. For example, the three sections 146, 148, 150 may be made from the same material but the first section is made thicker or has added ribs to render it more stiff and less flexible than the second and third sections. In another example, the first section 146 is made from a relatively more rigid material, a higher durometer, or a composite so that it is more rigid and stiff than the material and durometer used to form the second and third sections 148, 150. Thus, as structured, the valve 110 has three distinct valve sections, namely the first section 146, the second section 148, and the third section 150, and wherein the left and right sections, or first and second sides, of the second or third section 146 tend to be more pliable and flexible than the middle section 146. In an example, the middle section 146 functions as a seat for the second and third sections 148, 150 so that when the second and third sections 148, 150 rest or are pushed against the seat of the first section 146, the valve is in a position to restrict or limit flow through the catheter hub and across the valve 110. In some examples, the second and third sections are unitarily formed as a sub-valve body component with a space between two inner edges 254*a*, 254*b* of the second and third sections 148, 150 and a perimeter rim. The first section 146 is the attached to the sub-valve body component, such as by welding or gluing. In some examples, the first section 146 is co-molded, insert-molded, or over-molded to the sub-valve body component, which is formed with both the second and third sections. In yet another example, all three sections 146, 148, 150 are separately formed and subsequently attached together, such as by adhesive or bonding.

Each of the three sections 146, 148, 150 has one or more arcuate rim portions 202. When combined, the arcuate rim portions form a band 247 defining a circumference around the valve 110. The first section or middle section 146 of the valve 110 comprises an elongated body 204 having two opposing sides 206, 208 of generally equal chords and two opposing arcuate sections 212, 214. The arcuate sections 212, 214 are formed as part of or are arranged with the rim portions 202 of the valve 110. In one example, the second chord 208 is a mirror image of the first chord 206 with the second chord 208 running parallel to the first chord 206 but on the opposite side of the center 210 of the valve disk 110. In other examples, the opposing sides 206, 208 can have shaped edge surfaces to change the amount or extent of overlapping with the second 148 and third 150 sections, which can change the fluid flow space, as further discussed below. In other examples, the valve can embody multiple rigid sections spaced from one another and having a relatively more flexible section located between each pair of rigid sections to form more than two flow channels or paths. In a less preferred embodiment, the valve embodies a single rigid section and a single flexible section thereby forming a single flow path through the valve.

In an example, the first arcuate section 212 starts at a first end 230 of the first chord 206 and terminates at a first end 232 of the second chord 208, along the outer perimeter of the valve. The second arcuate section 214 starts at a second end 234 of the first chord 206 and terminates at a second end 236 of the second chord 208, along the opposing outer perimeter of the valve. The first section 146 is bowed along the length of the chords 206, 208, such that the first section bows outwardly in the proximal direction 50 (e.g., towards the viewer of FIG. 4A) to reach a point of maximum deflection at or near a point aligned with the center 210 of the elongated body 204 along the length of the chords, and then curves back towards the distal direction 52, e.g., the opposite direction, near the first 212 and second 214 arcuate sections, such that the points along the opposing arcuate sections 212, 214 rest in the same plane as the band 247 of the valve, as shown in FIG. 4A. Note that the terms first, second, third, etc. are understood to designate points or components that differ from other points or components only and are not structurally limiting unless the context indicates otherwise.

In an example, plurality of slits 218 defining plurality of flaps 236 are provided in or on the first section 146. In the example shown, three slits 218 are provided with different number of slits contemplated. The slits 218 can radiate from about the center 210 of the first section 146 with slits radiating from different points or locations on the middle section 146 contemplated. The slits 218 can be equally spaced around the center of the disk 210 and sized and shaped to receive a needle 12 (FIG. 1) for initial catheterization of the patient. The slits 218 can also allow fluid to flow into or out of the catheter hub 118 (FIG. 3) through the valve when the flaps 236 are deflected. For example, the flaps 236 can have surface features to allow them to flex outwardly in the proximal direction 50 (e.g., towards the viewer of FIG. 4A) when vacuum is applied at proximal opening of the catheter hub for drawing a sample across the valve. In an example, a pair of projections or shoulders can be provided on each flap 236 on the distal side 52 of the valve so that the flaps can flex in the proximal direction 50 but not the distal direction 52, which is prevented by the abutting pair of projections or shoulders. However, the elongate body 204 of the first section 204 is preferably made of a material of sufficient hardness, or is sufficiently thick or both, such that the slits 218, after the needle has been removed therefrom, will not open to allow fluid to pass through the slits 218 when the slits are subjected to standard IV fluid pressure flowing from a bag hung on a typical IV pole and connected to the catheter hub 118 (FIG. 3). In one example, flow pushed through the valve 110 and into the patient is provided through different flow arrangements across the valve 110 than flow being pulled through the catheter, such as during aspiration, by way of the slits and the flaps. Thus aspects of the present disclosure are understood to include a valve located inside a catheter hub and wherein the valve has multiple sections for multiple flow characteristics across the valve. For example, fluid flow from the distal direction 52 towards the proximal direction 50 may be through one part of the valve while flow from the proximal direction 50 towards the distal direction 52 may be through different part or parts of the valve. As disclosed, different flow paths through the valve 110 may be provided by selecting a material or a thickness that allows the flaps 236 and/or the second 148 section and the third section 150 to deflect without the use of an actuator or opener to open the valve through physical contacts.

The first section 146 may be made of any material suitable to provide a sealing function at the slits 218 upon closing after removal of the needle as shown in FIG. 4A, but still rigid enough to provide structural support for the second section 148 and the third section 150 as the second and third sections sway from a position spaced from the two chords 206, 208 to a position contacting or abutting the first section 146. The arrangement of the first 146, second 148 and third 150 sections is discussed in greater detail below and generally can be understood as having portions of the second and third sections moving away from and against the first section at points along the second and third sections that are not attached to the first section to either permit or limit fluid flow, or even stop fluid flow. In some embodiments, the first section 146 is made from a different material than the second 148 and third 150 sections. In other embodiments, the different sections 146, 148, 150 are made from the same material but have different dimensions or physical characteristics, such as different thicknesses and/or different durometers, which enable different functions at the different sections. Ribs or reinforcing features may also be added to the first section 146 so that the first section does not flex or sway due to fluid pressure, or at least does not flex or sway to the same extent as the second section 148 and the third section 150 so that fluid flow paths can be provided through the valve by way of different movements. The second and third sections are preferably made from the same material but different materials are contemplated. In some examples, the second section 148 and third section 150 are made from a material that is softer, or is more elastic, stretchable or flexible, than the material used to form the first section 146 so that differential pressure generally deflects the second and third sections only but not the first section. Exemplary flexible or stretchable material includes PTFE or silicone. Exemplary more rigid materials usable for the first section include many polymeric materials, such as natural rubber, synthetic rubber, polyethylene, polypropylene, and polyacrylonitrile. However, these materials can be arranged so that the valve can be made with any one or any combinations of the listed materials by incorporating different thicknesses, ribs, different durometers, or other flexible or rigid means, such as weakened sections, notches to form weakened sections, or other barriers to provide rigidity.

In an example, the second section 148 and the third section 150 are mirror images of one another and are defined by two edges 238a, 238b, with non-symmetry contemplated. The outer arcuate edge 238a of the second section 148 intersects the two endpoints 230, 234 of the first chord 206 and the outer arcuate edge 238b of the third section 150 intersects the two end points 232, 236 of the second chord 208. As further discussed below, the two arcuate edges 238a, 238b can extend past each respective chord so that the first and second chords 206, 208 overlap with inner edges 254a, 254b of the second 148 and third 150 sections. The second and third sections are further defined by a rim portion 202 and a flap portion 248. The rim portion 202 is defined by an outer edge 250 and an inner edge 252 and a band 247 formed therebetween. The flap portion 248 forms radially inwardly of the rim portion 202 and is shaped as an arcuate three-dimensional planar surface, similar to a surface of a sphere. Each flap portion 248 has an arcuate outer edge 246 that is coincident with the inner edge 252 of the rim portion 202. Each flap portion 248 has an inner or inside edge 254a, 254b that is located subjacent the middle section 146 near one of the two chords 206, 208. The flap portions 248 may sometime be referred to as first and second deflectable flap portions in that they can deflect or move under by fluid pressure. The arcuate planar surface of each flap section 248 extends outwardly towards the viewer in the proximal direction 50 so that the inner edge 254a, 254b of each flap section 248 pushes against the underside surface of the first section 146 near the two chords 206, 208 along the distal side 52 to close the fluid pathways defined by the two edges 254a, 254b and the two sides 206, 208, as further discussed below.

In some embodiments, the outermost edge 250 of the rim portion 202 may incorporate a bead to facilitate assembling the valve into the valve receiving space 162 (FIG. 3) of the catheter hub. In other embodiments the rim portion 202 may take on a generally concave appearance, and in still others the beads may be square or irregular, giving the generally flat section 247 the appearance of a flat or v-bottom groove, or a combination of the two. The shaped edge 238a, 238b, such as with a bead, when incorporated, is configured to assist with securing the valve 110 to the receiving space 162 inside the catheter hub.

With reference now to FIG. 4B, a top cross-sectional view of the valve 110 is shown. As previously described, a length L of the rim portion 202 and a surface section of each flap section 248 overlap the middle section 146 are shown. The arcuate rim portion 202 and the middle section 146 may be joined so that the two inner edges 254a, 254b of the second and third sections 148, 150 are in abutting contact with the middle section 146 to form two spaced apart seals that prevent or limit fluid passing through the valve, such as across the valve. However, along the length of the chords 206, 208 and the inner edges 254a, 254b of the two flap sections 148, the overlapped surfaces are not joined or connected, thereby creating flow paths 262a, 262b when the flap sections 148 are actuated, as further discussed below. When there is no fluid pressure at the proximal end of the catheter hub, the flap sections 148 are configured to recoil against the middle section 146 and close the flow paths 262a, 262b. Alternatively or in addition thereto, fluid pressure on the distal side can assist the flap sections 148 to recoil against the middle section to close the flow paths.

Although the valve 110 may be installed inside a catheter hub with just the arcuate rim portion 202, as shown, an extended rim portion 244 is optionally attached to the arcuate rim portion 202 as shown in FIG. 4B. The extended rim portion 244 has an arcuate outer perimeter 242 and together with the arcuate rim portion 202 and the flaps 148 define a concave cavity 264 located adjacent the convex spherical valve surface 266 defined by the three sections 146, 148, 150. The valve 110 may be attached to the valve receiving space 162 of the interior cavity 161 of the catheter hub 118 (FIG. 3). In an example, the arcuate rim portion 202 and the extended rim portion 244 of the valve 110, which are collectively referred to as the perimeter flange 270, snap into a corresponding shaped surface of the valve receiving space 162 to attach the valve 110 inside the catheter hub. In other examples, the catheter hub is made from a two-hub body and the rim portion 202, the extended rim portion 244, or the perimeter flange 270 is attached between the seams defined by the two hub-body forming the catheter hub.

With reference again to FIG. 4B, the convex side of the valve 110 may be referred to as an proximal side 272 or the first side 50 (FIG. 4A) and the concave side of the valve 110 may be referred to as a distal side 274. Further and as previously noted, the two flap portions 248 each comprises an inner edge 254a, 254b that overlaps with the middle section 146 and is made from a material that is relatively more flexible than the material used to form the middle section 140 of the valve. As such, the two flaps 248 are capable of moving when a sufficient differential pressure is present between the proximal side 272 and the distal side 274, such as when IV fluid is introduced in through the catheter hub of FIG. 3. Sufficient differential pressure will cause the two flap sections to move or bow at the inner edges 254a, 254b in the distal direction from the position shown in FIG. 4B. When this occurs, the flow paths 262a, 262b open to permit fluid to flow from the proximal end 272 to the distal end 274 through the valve 110 to infuse fluid to the patient. Thus, as shown, the present valve 110 is understood to include two elongated fluid paths 262a, 262b that extend roughly the length of each chord 206/208 and has a gap for fluid flow that can vary depending on the differential fluid pressure between the proximal end 272 and the distal end 274. When fluid pressure is higher at the proximal end than the distal end, the flap sections 248 will collapse along a mid-section 288 in the distal direction while the two ends of the flaps near the ends of the two chords, because they are attached, will be closed, such as in abutting contact with the middle section 146. When fluid pressure is higher at the distal end than the proximal end, the two flap portions will be pushed against the mid-section 110 and the two fluid paths 262a, 262b will close. The flap portions 248 can also recoil under their own elastic characteristics. In an example, each fluid path 262a, 262b has a gap that is non-uniform. In the present embodiment, each fluid path is narrow or is closed near the two ends of each chord 206, 208 and has a gap that is largest near a mid-point 288 between the two ends.

Thus, the flap portions 248 of the valve, which are positioned on each side of the middle section 146, may be understood to be movable between two positions. In the first position, the valve 110 is closed due to the pressure at the distal end 274 being higher than the pressure at the proximal end 272, which forces the two inner edges 254a, 254b of the two flaps 248 to press against the surface 276 of the first section 146 on the distal side, as shown in FIG. 4B. Alternatively or in addition thereto, the two flap portions 248 are biased against the first section under their own elastic characteristics. This closes the two fluid paths 262a, 262b thereby preventing fluid, such as blood, from freely flowing across the valve and out the proximal opening of the catheter hub. In the closed position, the flap portions 248 bow in the proximal direction and close against the elongate body 204 of the first or middle section 146 of the valve 110. In this position, the greater distal pressure presses the flap portions 248 against the elongate body 204 until the overlapping portions along length L contact the first or middle section 146 and the remainders of the two flap portions 248 adopt the general curvature of the valve disk 110. In this position, fluid is prevented or greatly restricted from flowing around the flap portions 248 or through the flow paths 262a, 262b and out the proximal opening of the catheter hub. Again, alternatively or in addition thereto, the two flap portions 248 are biased against the first section 146 under their own elastic characteristics to close the two flow paths 262a, 262b.

When sufficient fluid pressure is applied from the proximal side 272 of the valve 110, overcoming any residence pressure on the distal side 274, the two flap portions 248 will be displaced and move to a second position in which the flap portions 248 are deflected from their closed position, which is more clearly shown in FIGS. 5A-5C. Depending on the pressure differential between the proximal side 272 and the distal side 274, deflection occurs mainly at the two inner edges 254a, 254b of the flap portion 248 near the respective mid-sections 288, separating the straight edge 254a, 254b from the surfaces of the middle section 146 near the chords 206, 208, but leaving the flap portion 248 still bowed somewhat in the proximal direction. If the pressure differential is sufficiently great, the flap portions 248 may invert taking the shape of bowed sails in the distal direction 274.

When this occurs, the flap portions create even larger openings 262a, 262b at the two flow paths between the straight outer edges 254a, 254b of the flap portions 248 and the two chords 206, 208 of the first section 146. Under either opening scenario, the separation of the flap portions 248 from the elongated body 204 of the first section 146 allows fluid to flow from the proximal side 272 of the valve 110 to the distal side 274 through the two openings 262a, 262b formed by the flap portions 248 and the elongated body 204 of the first section 146. The two flow paths 262a, 262b adjacent the first chord 206 and the second chord 208 cause fluid to flow around the more rigid material of the elongated body 204, and specifically around the first chord 206 and the second chord 208, and through the openings 262a, 262b to infuse a patient with fluids, such as IV solutions and medicaments. In this way, the flap portions 248 create a one-way or check valve that depends on fluid pressure and pressure differential between the proximal side and the distal side. For example, when fluid pressure is higher at the proximal end 272 than the distal end 274, the valve will open to permit fluid flow through the two flow paths 262a, 262b. But when fluid pressure is higher on the distal side than the proximal side, such as when an IV line is disconnected from the proximal end of the catheter hub, the valve will close so that little or no fluid flow can flow in the proximal direction through the two flow paths 262a, 262b.

FIG. 4C shows a side cross-sectional view of the valve 110, which shows the first section 146 in cross-section and the flap portion 248 of the third section 150 in plan or side view. Also shown through the first section 146 are slits and flaps.

FIG. 5A shows a detailed perspective view of the valve of FIG. 4A in an open position. As shown, the flap portion 248 of the second section 148 and the flap portion 248 of the third section 150 are deflected in the distal direction 274 due to fluid pressure being greater on the proximal side, such as during IV transfusion with fluid pressure provided by gravity acting on a bag hanging on an IV pole. Because the first section or middle section 146 has a more rigid elongate body 204, it does not deflect or deflects less than the two flap portions 248 so that the flow paths 262a, 262b open to permit fluid to flow therethrough to infuse the patient.

FIG. 5B shows a top cross sectional view of the valve of FIG. 5A with the two flap portions 248 deflected and the two flow paths 262a, 262b open for fluid flow.

FIG. 5C shows a side cross sectional view of the valve of FIG. 5A.

While the exemplary embodiments shown here are generally circular in form, it is understood that one of ordinary skill in the art could contemplate other shapes, such as squares, rectangles, hexagons, or octagons, or any other regular or irregular polygon required to fit an interior of a catheter hub.

The present disclosure is further understood to include methods of manufacturing and methods of using the needle assemblies described.

Although limited embodiments of the control valve assemblies and their components have been specifically described and illustrated herein, many modifications and variations will be apparent to those skilled in the art. Furthermore, it is understood and contemplated that features specifically discussed for one control valve embodiment may be adopted for inclusion with another control valve embodiment, provided the functions are compatible. For example, the valve may be configured differently, having more or fewer sections. Accordingly, it is to be understood that the control valve assemblies and their components constructed according to principles of the disclosed device, system, and method may be embodied other than as specifically described herein. The disclosure is also defined in the following claims.

What is claimed is:

1. A needle assembly comprising:
   a needle hub;
   a needle extending from a distal end of the needle hub;
   a catheter tube attached to a catheter hub and having the needle extending through the catheter tube; and
   a valve positioned in an interior cavity of the catheter hub, said valve comprising a first section, a second section, and a third section,
      wherein the first section comprises a first side edge, a second side edge, and a plurality of slits defining a plurality of flaps,
      wherein a surface on the second section bows in a proximal direction and presses against the first section along a length of the first side edge in a valve closed position,
      wherein a surface on the third section bows in the proximal direction and presses against the first section along a length of the second side edge in the valve closed position, and
      wherein a first flow path is formed between the first section and the second section adjacent the first side edge by deflection of a first deflectable flap portion of the second section by a differential fluid pressure and a second flow path is provided between the first section and the third section adjacent the second side edge by deflection of a second deflectable flap portion of the third section by the differential fluid pressure.

2. The needle assembly of claim 1, wherein the valve is formed from at least two different materials.

3. The needle assembly of claim 2, wherein the plurality of slits comprise three slits located between the first side edge and the second side edge.

4. The needle assembly of claim 3, wherein each of the first side edge and the second side edge bow in the proximal direction.

5. The needle assembly of claim 2, wherein the material of the first section is more rigid than the material of the second section and the third sections.

6. The needle assembly of claim 1, wherein the surface on the second section forms an edge of the first deflectable flap portion and the surface formed on the third section forms an edge of the second deflectable flap portion.

7. The needle assembly of claim 6, wherein at least part of a surface of the first deflectable flap portion and at least part of a surface of the second deflectable flap portion are displaced from a first position to a second position when the valve is in an open position.

8. The needle assembly of claim 6, wherein the first deflectable flap portion overlaps the first side edge and the second deflectable flap portion overlaps the second side edge in the valve closed position.

9. The needle assembly of claim 1, further comprising a needle guard located inside the catheter hub, said needle guard being sized and shaped to cover a needle tip on the needle in a protective position.

10. The needle assembly of claim 1, wherein the first section has a width between the first side edge and the second side edge and a length defined between two arcuate edges at ends of the first side edge and the second side edge.

11. The needle assembly of claim 1, further comprising a rim portion circumscribing the first section, the second section, and the third section.

12. A method of manufacturing a needle assembly comprising:
    forming a needle hub and attaching a needle to the needle hub;
    attaching a catheter tube to a catheter hub, said catheter hub comprising an interior cavity;
    placing a valve comprising a first section, a second section, and a third section in the interior cavity of the catheter hub,
        wherein the first section comprises a first side edge and a second side edge,
        wherein the second section comprises a first deflectable flap portion having a surface that is in contact with the first section along a length of the first side edge, and
        wherein the third section comprises a second deflectable flap portion having a surface that is in contact with the first section along a length of the second side edge; and
    placing the needle through the first section of the valve and the catheter tube; and
    wherein deflection of the first deflectable flap portion at the first side edge defines a first flow path through the valve and deflection of the second deflectable flap portion at the second side edge defines a second flow path through the valve;
    wherein a surface on the second section bows in a proximal direction and presses against the first section along a length of the first side edge in a valve closed position, and wherein a surface on the third section bows in the proximal direction and presses against the first section along a length of the second side edge in the valve closed position.

13. The method of claim 12, wherein the valve is formed from at least two different materials.

14. The method of claim 12, wherein the first section of the valve comprises three slits sized and shaped to allow the needle to pass therethrough.

15. The method of claim 12, wherein the material of the first section is more rigid than the material of the second section and the third sections.

16. The method of claim 12, further comprising placing a needle guard over the needle to cover a needle tip of the needle in a protective position.

17. The method of claim 12, further comprising placing a male medical implement into a proximal opening of the catheter hub and using only fluid pressure to open the first flow path and the second flow path.

18. The method of claim 12, further comprising deflecting the second section and the third section in a distal direction to open the first flow path and the second flow path.

19. The method of claim 12, wherein the first section has a width between the first side edge and the second side edge and a length defined between two arcuate edges at ends of the first side edge and the second side edge.

20. The method of claim 19, wherein the length of the first section has a dimension that is larger than the width.

21. A needle assembly comprising:
    a catheter tube attached to a catheter hub and having a needle, which is attached to a needle hub, extending through the catheter tube; and
    a valve positioned in an interior cavity of the catheter hub, said valve comprising a rim portion having a first section, a second section, and a third section located within the rim portion,
        wherein the first section is located between the second section and the third section and the first section comprises a first side edge, a second side edge, and a plurality of slits defining a plurality of flaps,
        wherein a deflectable flap portion on the second section is pressed against the first section along a length of the first side edge,
        wherein a deflectable flap portion on the third section is pressed against the first section along a length of the second side edge, and
    wherein the deflectable flap portion on the second section and the deflectable portion on the third section bow in a proximal direction in a valve closed position and deflect in a distal direction when fluid pressure is applied in the interior cavity of the catheter hub.

* * * * *